(12) United States Patent
Fretard

(10) Patent No.: US 11,712,060 B2
(45) Date of Patent: Aug. 1, 2023

(54) WATER SMOKING PIPE DEVICE AND KIT

(71) Applicant: Lonny Fretard, Seaford, NY (US)

(72) Inventor: Lonny Fretard, Seaford, NY (US)

( * ) Notice: Subject to any disclaimer, the term of this patent is extended or adjusted under 35 U.S.C. 154(b) by 166 days.

(21) Appl. No.: 17/192,212

(22) Filed: Mar. 4, 2021

(65) Prior Publication Data

US 2021/0274834 A1 Sep. 9, 2021

Related U.S. Application Data

(60) Provisional application No. 62/985,551, filed on Mar. 5, 2020.

(51) Int. Cl.
*A24F 1/14* (2006.01)
*A24F 1/30* (2006.01)
*A61B 17/17* (2006.01)

(52) U.S. Cl.
CPC .............. *A24F 1/14* (2013.01); *A24F 1/30* (2013.01); *A61B 17/17* (2013.01)

(58) Field of Classification Search
CPC .............. A24F 1/14; A24F 1/30; A61B 17/17
See application file for complete search history.

(56) References Cited

U.S. PATENT DOCUMENTS

2016/0270439 A1\* 9/2016 Webber ............... A24F 1/30
2017/0099872 A1\* 4/2017 Reimann ............. A24F 1/30

OTHER PUBLICATIONS

OldHippie."MakeYourOwnGlassBong,Part3:HowToDoIt."BeyondChronic,Oct. 24, 2012.Web.. (Year: 2012).\*
EAB ("How to Use a Diamond Hole Saw", Jun. 14, 2017, <https://www.youtube.com/watch?v=PjlJRNPl5o> (Year: 2017).\*

\* cited by examiner

*Primary Examiner* — Michael J Felton
*Assistant Examiner* — Ronnie Kirby Jordan
(74) *Attorney, Agent, or Firm* — Shore IP Group, PLLC; Sean R. Wilsusen, Esq.

(57) ABSTRACT

A kit for use in forming a water pipe includes a glass tube defining a bowl housing at a proximal end thereof and a smoke outlet at a distal end thereof. The glass tube is configured for insertion into a bottle. A grommet is configured for positioning in a sidewall of the bottle. The grommet is configured to receive the glass tube therethrough. A drill bit is configured for forming a hole in the sidewall of the bottle. The hole is configured to receive the grommet therein. A drill bit guide is configured to be secured against the sidewall of the bottle. The drill bit guide is configured to guide a path of the drill bit as the drill bit forms the hole in the sidewall of the bottle.

14 Claims, 3 Drawing Sheets

WATER SMOKING PIPE DEVICE AND KIT

CROSS-REFERENCE TO RELATED APPLICATION

The present application claims the benefit of and priority to U.S. Provisional Application No. 62/985,551, filed Mar. 5, 2020. The entire contents of which are incorporated by reference herein.

INTRODUCTION

The disclosure relates a smoking pipe and, more particularly, to a water smoking pipe and a kit for forming the water smoking pipe.

BACKGROUND

A water smoking pipe is a filtration device, similar to a hookah, employed for smoking tobacco. A water smoking pipe may be constructed from any vessel that is airtight or watertight. The water smoking pipe may be formed by adding a bowl and stem apparatus (e.g., a slide) which guides air and smoke downward below a water level in the vessel. The smoke passes through the water and is cooled prior to entering an interior of the vessel above the water level. Generally, water smoking pipes employ a straight bowl and stem apparatus inserted at an angle into the vessel.

SUMMARY

In accordance with an aspect of the disclosure, a kit for use in forming a water pipe includes a glass tube defining a bowl housing at a proximal end thereof and a smoke outlet at a distal end thereof. The glass tube is configured for insertion into a bottle. A grommet is configured for positioning in a sidewall of the bottle. The grommet is configured to receive the glass tube therethrough. A drill bit is configured for forming a hole in the sidewall of the bottle. The hole is configured to receive the grommet therein. A drill bit guide is configured to be secured against the sidewall of the bottle. The drill bit guide is configured to guide a path of the drill bit as the drill bit forms the hole in the sidewall of the bottle.

In some aspects, the glass tube defines a first curve and a second curve along a length of the glass tube.

In some aspects, a bowl head is configured for insertion into the bowl housing of the glass tube.

In some aspects, the grommet includes an outer securing flap, an inner securing flap, and a connecting member connecting the outer securing flap and the inner securing flap. A passageway is defined through the grommet. The passageway is configured to receive the glass tube therethrough. The grommet may include or may be formed of rubber or plastic.

In some aspects, the drill bit guide is a removable stick-on guide.

In some aspects, the drill bit is a glass drill bit. The drill bit may be a diamond drill bit configured to drill through glass.

In some aspects, the bottle is a glass bottle.

In some aspects, an instruction pamphlet provides instructions for forming the water pipe.

In accordance with an aspect of the disclosure, a water pipe includes a bottle and a grommet disposed in a sidewall of the glass bottle. The grommet defines a passageway between an outside of the bottle and an inner chamber of the bottle. A glass tube defines a bowl housing at a proximal end thereof, a smoke outlet at a distal end thereof and a central region extending through the passageway of the grommet. The smoke outlet is positioned in the inner chamber of the bottle and the bowl housing is positioned outside the bottle. The glass tube defines a first curved portion positioned in the inner chamber of the bottle and a second curved portion positioned outside the bottle.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
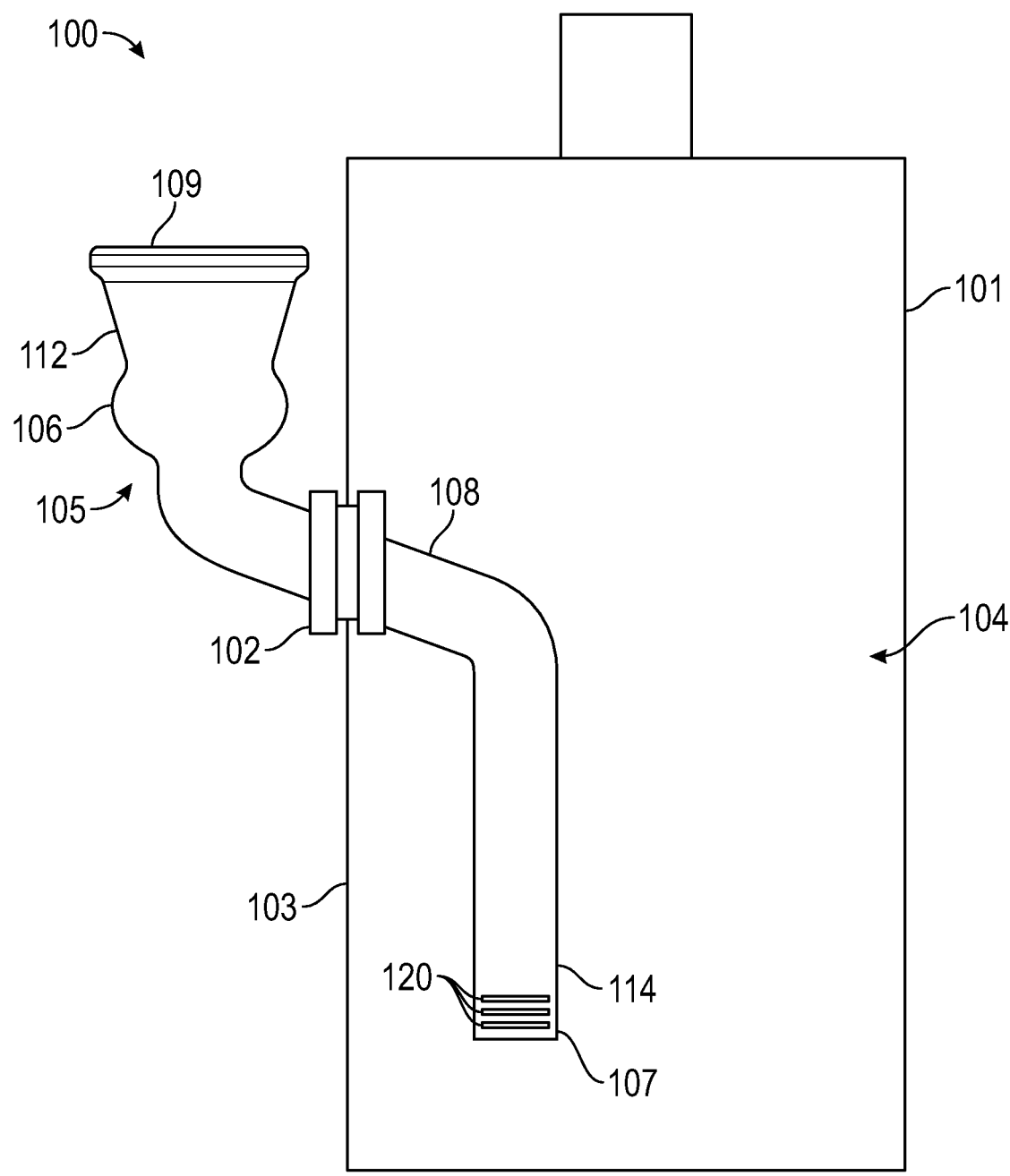
FIG. 1 is a side view of a water smoking pipe in accordance with the disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

"About" or 'approximately' or "substantially" as used herein may be inclusive of the stated value and means within an acceptable range of variation for the particular value as determined by one of ordinary skill in the art, considering tolerances (e.g., material, manufacturing, use, environmental, etc.) as well as the measurement in question and the error associated with measurement of the particular quantity (e.g., the limitations of the measurement system).

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings). Like reference numerals may refer to like elements throughout the specification and drawings.

Figures 2, 3A:
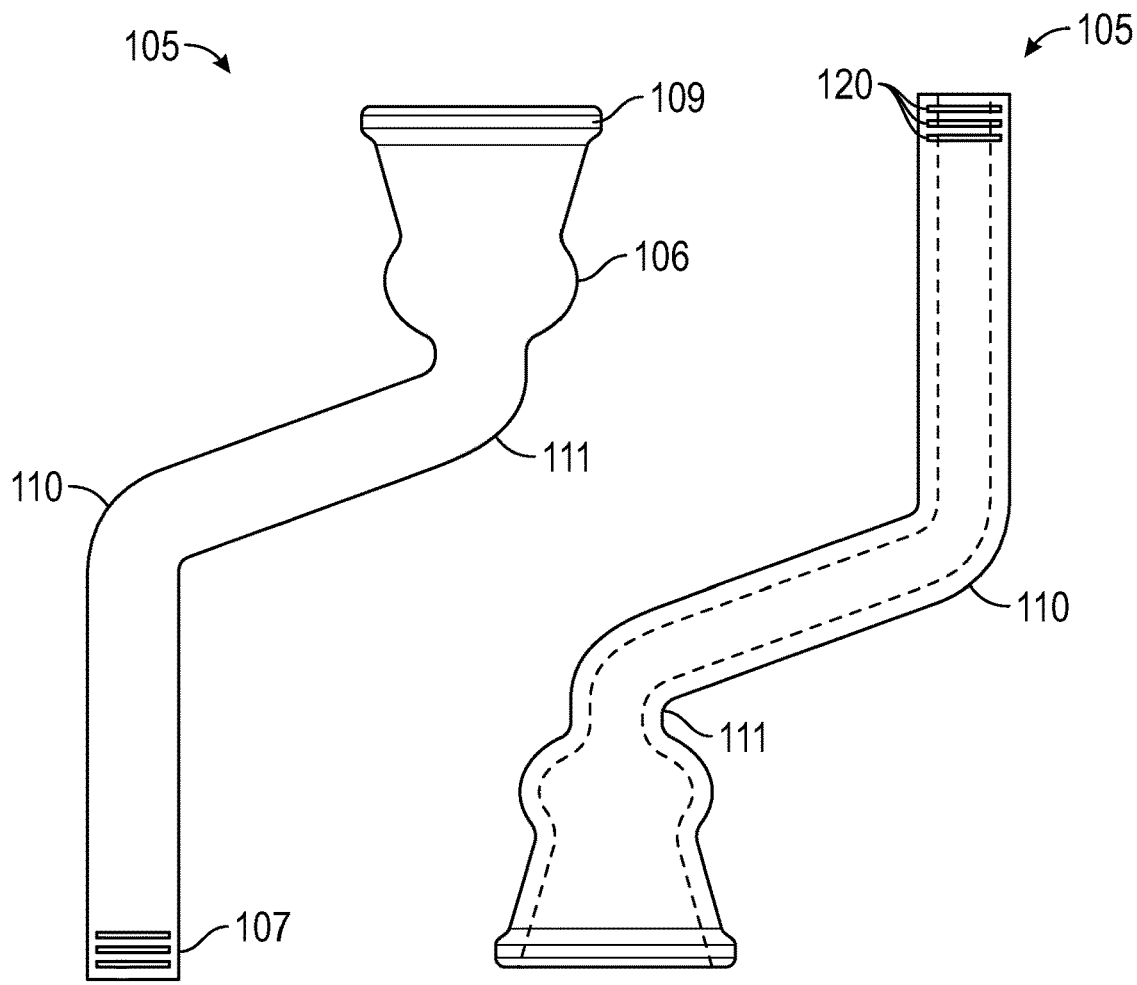
FIG. 2 is a side view of a glass tube in accordance with the disclosure.
FIG. 3A is a side view of a glass tube in accordance with the disclosure.
Figure 3B:
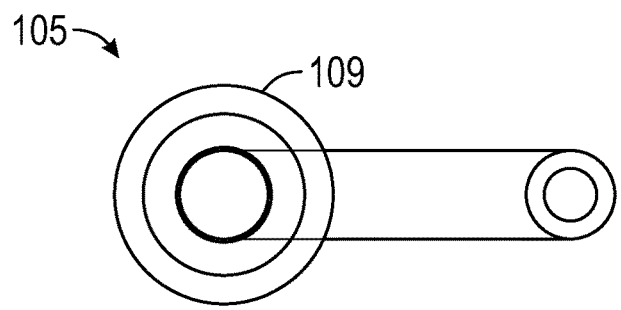
FIG. 3B is a conceptual diagram of a bowl insert in accordance with the disclosure.
Figure 4:
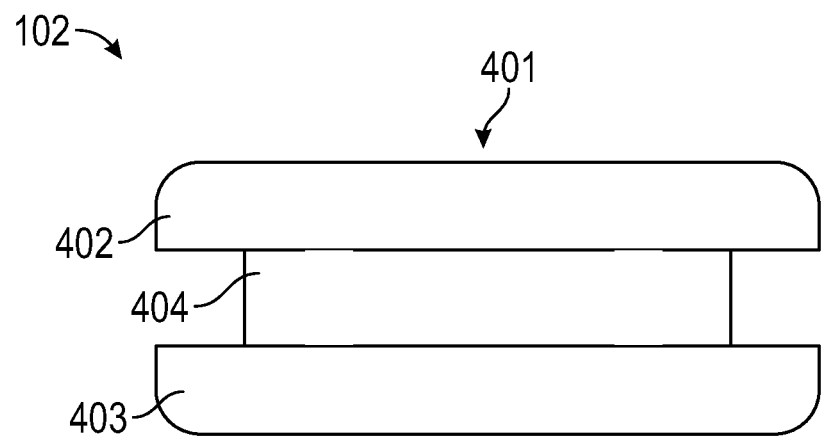
FIG. 4 is a side view of a grommet in accordance with the disclosure.
Figure 5:
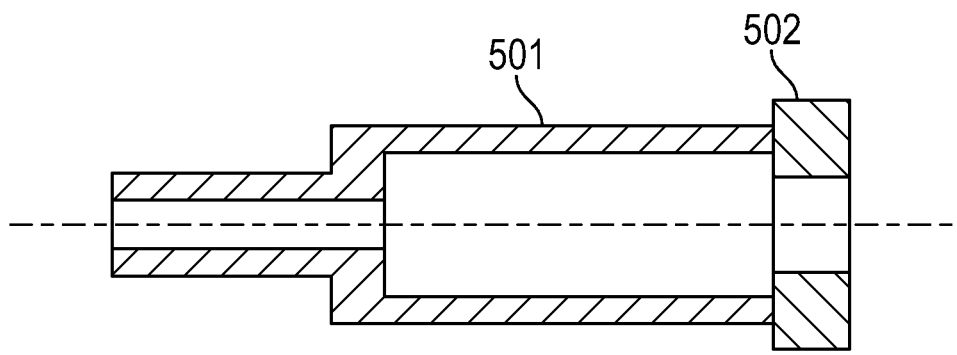
FIG. 5 is a side view of a drill bit and a drill bit guide in accordance with the disclosure.

Referring to FIGS. 1-5, in accordance with an aspect of the disclosure, a kit for use in forming a water pipe 100 includes a glass tube 105 defining a bowl housing 106 at a proximal end 112 thereof and a smoke outlet 107 at a distal end 114 thereof. The glass tube 105 is configured for insertion into a bottle 101. A grommet 102 is configured for positioning in a sidewall 103 of the bottle 101. The grommet 102 is configured to receive the glass tube 105 therethrough. A drill bit 501 is configured for forming a hole in the sidewall 103 of the bottle 101. The hole is configured to receive the grommet 102 therein. A drill bit guide 502 is configured to be secured against the sidewall 103 of the bottle 101. The drill bit guide 502 is configured to guide a path of the drill bit 501 as the drill bit 501 forms the hole in the sidewall 103 of the bottle 101.

In an exemplary embodiment, the glass tube 105 defines a first curve 110 and a second curve 111 along a length of the glass tube 105. The first curve 110 may be positioned outside the bottle 102, and the second curve 111 may be positioned inside the bottle 101.

In some aspects, the shape of the glass tube 105 may position the bowl housing 106 such that an upper level of the bowl housing 106 is substantially parallel with a bottom surface of the bottle 101. Thus, the upper level of the bowl housing 106 is substantially level. A bowl head 109 is configured for insertion into the bowl housing 106 of the glass tube 105. As a result of the shape of the glass tube 105, the bowl head 109 may also be positioned in a substantially level position, such that an upper surface of the bowl head 109 rests along a plane parallel to a bottom surface of the bottle 101. This prevents tobacco from falling out of the bowl head 109 during use, as compared with a bowl head positioned at an angle with respect to the bottom surface of the bottle 101.

In some aspects, the glass tube 105 is shaped and dimensioned such that a distal end portion 114 of the glass tube 105 is below an upper level of water housed in an inner chamber 104 of the bottle. The smoke outlet of the glass tube may include a plurality of slits 120 formed at a distal end portion 114 of the glass tube 105. The slits 120 increase air flow through the smoke outlet 107 and prevent clogging of the smoke outlet 107.

The particular angles of the first and second curves 110 and 111 of the glass tube 105 may be modified, as desired. For example, the first curve 110 may define a first angle of curvature, while the second curve 111 defines a second angle of curvature different from the first angle of curvature.

In some aspects, the glass tube 105 defines a continuously open inner lumen (see, e.g., FIG. 3A) configured to pass smoke from the bowl housing 106 and into the inner chamber 104 of the bottle 101.

In an exemplary embodiment, the grommet 102 includes an outer securing flap 402, an inner securing flap 403, and a connecting member 404 connecting the outer securing flap 402 and the inner securing flap 403. The connecting member 404 may be narrower than the outer and/or inner securing flaps 402 and 403. The connecting member 404 may traverse the hole drilled in the sidewall 103 of the bottle 101, and the outer and inner securing flaps 402 and 403 prevent the grommet 102 from moving. A passageway 401 is defined through the grommet 102. The passageway 401 includes a hole extending through the connecting member 404 from an outside of the bottle 101 to the inner chamber 104 of the bottle 101. The passageway 401 is configured to receive the glass tube 105 therethrough. The grommet 102 performs the function of preventing damage to the bottle 101 and holds the glass tube 105 in a desired position. The grommet 102 also facilitates removal of the glass tube 101, as desired, such as for cleaning or maintenance of the bottle 101.

The grommet 102 may include or may be formed of rubber or plastic. The grommet 102 is sufficiently flexible to allow insertion of the glass tube 105 through the grommet 102 after the grommet 102 is positioned in the sidewall 103 of the bottle 101. Additionally, the flexibility of the grommet 102 allows removal of the glass tube 105 therefrom, as desired.

In an exemplary embodiment, the drill bit guide 502 is a removable stick-on guide. For example, the drill bit guide 502 may include an adhesive surface below an outer covering. The outer covering may be removed, and the drill bit guide 502 may then be removably adhered to an outer surface of the bottle 101. The drill bit guide 502 prevents that drill bit 501 from damaging (e.g., cracking) the bottle 101 when the hole in the sidewall 103 of the bottle 101 is formed.

In an exemplary embodiment, the drill bit 501 is a glass drill bit. The drill bit 501 may be a diamond drill bit configured to drill through glass. As an example, the drill bit 501 may be formed of or may include metal. The drill bit 501 may be a 13 mm bit; however, exemplary embodiment is not limited thereto, and drill bits of other sizes may be employed.

In use, wetting the outer surface of the bottle 101 while the hole is drilled may prevent damage from occurring to the bottle 101.

In some aspects, the bottle 101 is a glass bottle. For example, any desired glass bottle may be retrofitted to form the water smoking pipe using the kit and/or methods described herein. The glass bottle 101 may include a top spout or opening use to inhale smoke having passed through the glass tube 105 and into the inner chamber 104 of the bottle 101.

In some aspects, an instruction pamphlet provides instructions for forming the water pipe 100. The instruction pamphlet may be a printed set of paper instructions for how to use the kit described herein (e.g., by retrofitting a bottle to form the water smoking pipe 100 described herein without damaging the bottle).

In accordance with an aspect of the disclosure, a water pipe 100 formed using the kit described herein includes the bottle 101 and the grommet 102 disposed in the sidewall 103 of the bottle 101. The grommet 102 defines a passageway 401 between an outside of the bottle and an inner chamber 104 of the bottle 101. The glass tube 105 defines a bowl housing 106 at the proximal end 112 thereof, the smoke outlet 107 at a distal end 114 thereof and a central region 108 extending through the passageway 401 of the grommet 102. The smoke outlet 107 is positioned in the inner chamber 104 of the bottle 101 and the bowl housing 106 is positioned outside the bottle 101. The glass tube 105 defines the first curved portion 110 positioned in the inner chamber 104 of the bottle 101 and a second curved portion 111 positioned outside the bottle 101.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A kit for use in forming a water pipe, comprising:
   a glass tube defining a bowl housing at a proximal end thereof and a smoke outlet at a distal end thereof, the glass tube configured for insertion into a bottle, wherein the glass tube defines a first curve and a second curve along a length of the glass tube;

a grommet configured for positioning in a sidewall of the bottle, the grommet configured to receive the glass tube therethrough;

a drill bit configured for forming a hole in the sidewall of the bottle, the hole configured to receive the grommet therein; and a drill bit guide configured to be secured against the sidewall of the bottle, the drill bit guide configured to guide a path of the drill bit as the drill bit forms the hole in the sidewall of the bottle.

2. The kit of claim 1, further including a bowl head configured for insertion into the bowl housing of the glass tube.

3. The kit of claim 1, wherein the grommet includes an outer securing flap, an inner securing flap, and a connecting member connecting the outer securing flap and the inner securing flap, and wherein a passageway is defined through the grommet, the passageway configured to receive the glass tube therethrough.

4. The kit of claim 1, wherein the grommet includes rubber or plastic.

5. The kit of claim 1, wherein drill bit guide is a removable stick-on guide.

6. The kit of claim 1, wherein the drill bit is a glass drill bit.

7. The kit of claim 1, wherein the drill bit is a diamond drill big bit configured to drill through glass.

8. The kit of claim 1, wherein the bottle is a glass bottle.

9. The kit of claim 1, further including an instruction pamphlet providing instructions for forming the water pipe.

10. A kit for use in forming a water pipe, comprising:
a glass tube defining a bowl housing at a proximal end thereof and a smoke outlet at a distal end thereof, the glass tube configured for insertion into a bottle, wherein the glass tube defines a first curve and a second curve along a length of the glass tube, wherein the first curve is configured to be arranged outside the glass bottle when the glass tube is received within the grommet, and wherein the second curve is configured to be arranged inside the glass bottle when the glass tube is received within the grommet;

a grommet configured for positioning in a sidewall of the bottle, the grommet configured to receive the glass tube therethrough;

a drill bit configured for forming a hole in the sidewall of the bottle, the hole configured to receive the grommet therein; and a drill bit guide configured to be secured against the sidewall of the bottle, the drill bit guide configured to guide a path of the drill bit as the drill bit forms the hole in the sidewall of the bottle.

11. The kit of claim 10, wherein a first angle of curvature defined by the first curve is different from a second angle of curvature defined by the second curve.

12. A kit for use in forming a water pipe, comprising:
a glass tube defining a bowl housing at a proximal end thereof and a smoke outlet at a distal end thereof, the glass tube configured for insertion into a bottle, a grommet configured for positioning in a sidewall of the bottle, the grommet configured to receive the glass tube therethrough;

a drill bit configured for forming a hole in the sidewall of the bottle, the hole configured to receive the grommet therein;

a drill bit guide configured to be secured against the sidewall of the bottle, the drill bit guide configured to guide a path of the drill bit as the drill bit forms the hole in the sidewall of the bottle; and a bowl head configured for insertion into the bowl housing of the glass tube, wherein the bowl housing is configured to position the bowl head along a first plane substantially parallel with a second plane defined by a bottom surface of the glass bottle.

13. The kit of claim 1, further including a plurality of slits defined at the distal end of the glass tube.

14. The kit of claim 13, wherein the glass tube is configured to position the plurality of slits below a water line defined by the glass bottle.

* * * * *